United States Patent [19]

Zamola et al.

[11] 4,133,716
[45] Jan. 9, 1979

[54] METHOD FOR THE BIOSYNTHESIS OF A MICROBIAL INSECTICIDE

[75] Inventors: Branimir Zamola, Chiasso; Franjo Kajfež, Lugano, both of Switzerland

[73] Assignee: CRC Compagnia Ricerca Chimca, S.A., Chiasso, Switzerland

[21] Appl. No.: 744,102

[22] Filed: Nov. 22, 1976

[51] Int. Cl.² .......................... C12J 5/00; C12B 1/08; A01N 15/00

[52] U.S. Cl. ........................................ 195/96; 195/59; 424/93

[58] Field of Search ....................... 195/96, 59; 424/93

[56] References Cited

U.S. PATENT DOCUMENTS

| | | | |
|---|---|---|---|
| 3,073,749 | 1/1963 | Megna | 195/96 |
| 3,086,922 | 4/1963 | Mechalas | 195/96 |
| 3,087,865 | 4/1963 | Drake et al. | 195/96 |

OTHER PUBLICATIONS

Schaeffer, Bacteriological Reviews, vol. 33, No. 1, pp. 48-71 (1969).

*Primary Examiner*—Thomas G. Wiseman
*Attorney, Agent, or Firm*—Haseltine, Lake, & Waters

[57] ABSTRACT

A method for the biosynthesis of a microbial insecticide containing spores and crystalline endotoxin, in which a *Bacillus thuringiensis* microorganism is cultivated in a nutrient medium under formation of spores in such a way that the early lysis of the cells caused in the course of the submerged cultivation by the ventilation prior to the end of the formation of spores is prevented, is described.

2 Claims, No Drawings

METHOD FOR THE BIOSYNTHESIS OF A MICROBIAL INSECTICIDE

The present invention relates to a novel method for the biosynthesis of a microbial insecticide containing spores and crystalline endotoxin, said method being characterized in that the *Bacillus thuringiensis* microorganism or a related bacillus is cultivated in a nutrient medium under formation of spores in such a manner that the early lysis of cells caused in the course of the submerged cultivation by the ventilation prior to the termination of the formation of spores is prevented.

It is known that the early lysis of cells in the course of the cultivation leads to low yields and a reduced effectiveness of the bioinsecticide as well as to an increase of its toxicity.

The present invention provides for an improved method of producing spores and crystalline endotoxin in the process in which the early lysis of bacteria cells normally occurs as a result of enzymatic actions which are induced by the ventilation.

The delay in the formation of spores during the vegetative growth of bacteria is attributed to the effect of one or several inhibitors of an albuminous nature. The proteolytic decomposition of suggested inhibitors initiates the formation of the spores. Furthermore, various theories relating to the function of the protease have been submitted which is one of the early manifestations connected with the begin of spore formation (J. Mandelstam and W. M. Waites, Biochem.J., volume 109, pp. 793 to 801, 1968). According to Schaeffer, it has been suggested that in the course of growth of bacteria in a quickly metabolized nutrient substrate and in the presence of a usuable nitrogen source, metabolic products occur which would suppress the synthesis of extracellular proteases and an enzyme that is specific to the formation of spores, possibly in a manner similar to what is happening in the cancer cycle (P. Schaeffer, Bacteriol, Rev., volume 33, pp. 48 to 71, 1969). The result of such a suppression is the accumulation of acetic acid and pyroracemic acid which causes a decline of the pH and the early lysis of bacteria cells in general.

Now, according to a preferred execution of the present invention it is possible in connection with the sporulation to prevent the early lysis of bacteria cells by carrying out the biosynthesis for 4 to 6 hours under anaerobic conditions, and maintaining the pH in the course of the biosynthesis within the range of 6.3 to 7.

With the help of the present invention it was possible to recover, among other things, the parasporal protein crystal bodies ($\sigma$-endotoxin), and to purify the same by removing therefrom the water-soluble exotoxin ($\beta$-exotoxin) which must be removed because of its toxicity to mammals. The best method for removing the exotoxin, according to the present invention, comprises the use of semi-permeable diaphragms.

It is known that the *Bacillus thuringiensis*-group of microorganisms is characterized by the formation of protein-containing parasporal endotoxin crystals. The insect-pathogenic nature of *Bacillus thuringiensis* on a large row of lepidopterous larvae by ingestion is primarily to be attributed to the effect of endotoxin. Certain strains of *Bacillus thuringiensis*, in addition to intracellular endotoxin, form an extracellular, water-soluble exotoxin which is stable under heat. The term exotoxin relates in this case to an active substance of living cells which is discharged or secreted into the medium while the endotoxin contrary thereto is set free only after the cells have been completely dissolved.

So as to facilitate a better understanding of the present invention the characteristics of the above-mentioned toxins are described in greater detail as follows:

The Crystalline Endotoxin

A protein-containing crystalline inclusion has been isolated from the sporulated culture of *Bacillus thuringiensis* by Hannay and Fitz-James (C. L. Hannay and P. Fitz-James, Can.J. Microbiol., volume 1, pp. 694 to 710, 1955). The electron-microscopic studies have shown that in the course of the formation of spores of bacillus thuringiensis bacteria, an asporal crystalline body was developed together with the spores. It was concluded that a new relation exists between the formation of the spores and the endotoxin crystals. Recent research indicated that the crystalline endotoxin is composed of a high molecular protein component and a silicon skeleton. The spores and the endotoxin crystals may be recovered from the culture medium in the sediment of a high-speed centrifuge. The separation of the crystalline endotoxin from the spores was achieved in different ways, e.g. by fractionated sedimentation, step-by-step sedimentation, and separation in a two-phase system.

The Exotoxin

In addition to the crystalline endotoxin, certain *Bacillus thuringiensis* strains secrete in the course of the vegetative growing phase a toxic fraction into the medium which is chemically related to the adenine nucleotides. No relation exists between the generation of crystalline endotoxin and exotoxin. According to tests, exotoxin can be formed only by defined generic types of special *Bacillus thuringiensis* varieties. The method of producing exotoxin has been developed by De Barjac. According to said method, *Bacillus thuringiensis* is cultivated in a medium containing mineral salts in addition to 0.75% peptone and 1% glucose, namely for 70 hours at 30° C.

The preparation of microbial insecticides according to the present invention is preferably carried out in the following stages:

(A) Cultivation

The cultures are obtained based on the spores of a strain of *Bacillus thuringiensis bacteria. (ATCC* 10792 E. A. Steinhaus-O. Mattes) (N. R. Smith USDA 996), From Mediterranean Flour Moth, Ephestia Kuehniela, USDA MISC., PUBL. 559:51(1946) USDA Agr. Monogr. 16:67 (1952).

The nutrient medium for preparing the vegetative inoculum in shaking bottles contains the following components:

| | |
|---|---|
| bacto-trypton ("Difco") | 0.8% by weight |
| glucose | 2.5% by weight |
| $MgSO_4 \cdot 7H_2O$ | 0.2% by weight |
| $ZnSO_4 \cdot 7H_2O$ | 0.2% by weight |
| $Fe_2(SO_4)_3$ | 0.2% by weight |
| $MnSO_4 \cdot 5H_2O$ | 0.1% by weight |

The medium for agar slant cultures was the same as above but including also an addition of 2% agar.

Good results have been obtained with the cultivation in the following media:

| Medium I: | |
|---|---|
| molasses (50% solid material) | 1.4% by weight |
| yeast | 0.3% by weight |

-continued

| Medium I: | |
|---|---|
| (NH$_4$)$_2$SO$_4$ | 0.1% by weight |
| C.S.L. (maize-macerating liquid) | 0.1% by weight |
| CaCO$_3$ | 0.1% by weight |

The pH after the sterilization was 6.8.

Or with the medium containing starch instead of molasses:

| Medium II: | |
|---|---|
| starch | 1.3% by weight |
| yeast | 1.0% by weight |
| Na$_2$HPO$_4$ | 0.4% by weight |
| C.S.L. (maize-macerating liquid) | 0.2% by weight |
| CaCO$_3$ | 0.8% by weight |

The pH after sterilization was 6.8.

The nutrient medium for the vegetative inoculum (300 ml) was contained in sterilizable bottles with flat bottoms and 1 liter filling capacity. The nutrient medium contained in said bottles was sterilized for 45 minutes at 121° C. The glucose was sterilized separately according to the Tindalization method and aseptically added to the sterilized medium. The nutrient medium for the cultivation in the fermentators was prepared and sterilized in portions in the fermentator for 45 minutes at 121° C. Cultivation was carried out in fermentators made of stainless steel. The culture was rotated at 150 r.p.m.; ventilated with 0.5 liter per liter of culture per minute; the incubation temperature was from 28 to 30° C. The application of an "anaerobic shock" was carried out by discontinuing the ventilation for 3 to 6 hours in the 12th hour of the submerged cultivation. The timing for interrupting the ventilation was achieved with the help of an oxygen analyzer. The cultivation may be carried out without any early lysis of cells and without applying the afore-stated "anaerobic shock" if in the course of the cultivation the pH is regulated in such a way that it will not fall below 6.3. The formation of spores and the simultaneous setting free of endotoxin crystals ends after 35 to 40 hours of cultivation.

(B) Separation and Purification

After the bacteria have completely dissolved while spores and endotoxin crystals have been set free at the same time, the separation of the spores and the crystalline endotoxin from the exotoxin is carried out. Water-soluble exotoxin is preferably removed by means of dialysis. This method results in a mixture of spores and crystalline endotoxin which is not toxic to mammals. The presence or absence of water-soluble exotoxin was determined by the biological test described by Bond et al. A nutrient medium for the biological test was prepared by heating the mixture comprising 10 g pulverized agar, 500 ml fresh milk, and 7 g yeast. A 10 ml-sample was subsequently placed into a Petri dish having a diameter of 9 cm and filled already with 250 u liter of the test solution. As soon as the gels had solidified, 20 eggs of musca domestica were added. The plates were kept for 48 hours in an incubator at 30° C., and the development of larvae and the disturbance of the agar gel were observed (R. P. M. Bond, C. B. C. Boyce and S. J. French, Biochem.J., volume 114, pp. 477 to 488, 1969). The resulting product, which is freed from water-soluble exotoxin, may be processed and used in the customary manner for the preparation of insecticides.

(C) Drying

The drying step may be carried out according to any one of the following methods:

By admixing the resulting mixture comprising spores and endotoxin crystals with Bentonitic clays and placing the blend in the form of thin films in a ventilated dryer equipped with plates, at a temperature of about 40 to 45° C.;

by suspending the resulting mixture in water and drying in a rotating or pneumatic dryer;

by spraying the resulting mixture in a spray dryer.

(D) Crushing and Screening

If the mixture is dried in a spray dryer the resulting product requires no further crushing. When drying the mixture in ventilated dryers on plates, the product is crushed in a device of the Alpina type and screened using a sieve with a fine mesh conforming at least to mesh No. 180.

(E) Determination of the Effectiveness

The effectiveness was determined according to the following methods: by counting the living spores present according to the plate method and by carrying out bio-tests on test insects.

The resulting products are normed according to the standards established by the French Laboratoires de Lutte Biologique et de Biocinetique de la Miniere (I.N.-R.A.).

The present invention will be more clearly understood with the help of the description of the following examples which, however, do not in any way constitute any limitation of the present invention:

EXAMPLE 1

Based on the Berliner variety of the *Bacillus thuringiensis* culture, the cultivation is carried out according to the method herein described using a liquid, ventilated medium, namely medium I (see above). The incubation temperature applied in the course of the submerged cultivation is about 28° C. The culture is put into motion at 150 r.p.m.; the rate of ventilation is 0.5 liter per liter per minute. The ventilation is interrupted for 3 to 6 hours in the 12th to 14th hour of cultivation. The timing for interrupting the ventilation was determined with the help of an oxygen analyzer; ventilation was interrupted as soon as the percentage of solubility and the oxygen consumption decreased, and the pH fell to about 5.8. After from 3 to 6 hours, the ventilation was continued at the same rate of 0.5 liter per liter per minute. The cultivation without early lysis may be carried out without anaerobiosis if the pH of the medium is maintained within the range of 6.3 to 6.5. The submerged cultivation is continued until the spores and the crystalline endotoxin are yielded or transferred into the medium (35 to 40 hours on the average). The culture medium is subsequently placed into the receptacle in which the purification is carried out by removing the water-soluble exotoxin. Said purification takes place by means of dialysis. For this purpose it is possible to use a device as shown in the enclosed FIGURE. The culture medium is transferred from the fermentator to receptacle A which is equipped with an agitator e and a dialysis diaphragm a. This diaphragm may be colloidal or of any type as customarily used in practical life. The dialysis takes place more rapidly if deionized water b is added to receptacle B. The presence of absence of water-soluble exotoxin is determined by the afore-described bio-test. A powdery filling material is added to the resulting mixture of spores and crystalline endotoxins, and the mixture is then dried in a drying kiln on plates. The resulting product is ground in a crusher of the Alpina type, and then screened in order to obtain a powder.

EXAMPLE 2

The method is carried out as defined in Example 1, however, the nutrient medium II (see above) is used for the submerged cultivation in the fermentator.

EXAMPLE 3

The method is carried out as defined in Example 1, however, after the submerged cultivation of the bacteria and execution of the dialysis, i.e. after the exotoxin has been removed, the resulting product in dried in a centrifugal dryer and subsequently ground in an Alpina mill.

EXAMPLE 4

The method is carried out as defined in Example 1, however, the product obtained after the submerged cultivation of the bacteria and execution of the dialysis is suspended again in a defined amount of water, and this suspension is spray-dried in a spray dryer. The temperature within the dryer was from 90 to 100° C. The best suitable devices for this purpose are spray dryers equipped with disks which rotate at from 10,000 to 15,000 r.p.m. The product is a very fine powder which needs neither grinding nor screening. The exotoxin is not present in this end product.

The present invention may be applied or utilized also for other varieties of the same type of bacteria, for example the sotto variety of *Bacillus thuringiensis*, the subtoxicus variety of *Bacillus thuringiensis*. All these bacteria are described in detail in the relevant literature.

One advantage of the present invention lies in the higher effectiveness of the resulting product and the excellent purity of this product with respect to exotoxin combined with high yields of spores and crystalline endotoxins.

Insecticidal Activity of the Active Component, BACTUCIDE

The insecticidal activity of the active component embracing the spores of the *Bacillus thuringiensis* bacteria bacteria and the crystal endotoxin can be regarded in two ways:

- as the number of spores of *Bacillus thuringiensis* bacteria in a gram of the active component, and
- as international units (IU). The active component as a part of our formulations, shows the following activity:

$10^{10}$ spores/g of active component;

6000 and 15,000 IU/mg of the active component.

1000 IU/mg is the value of the product showing the same insecticidal activity as a standard sample E-61 (a mixture of spores and crystals of endotoxin of *Bacillus thuringiensis* bacteria tested on the insect Ephestia Kuhniella). With the active component the following formulations are prepared:

| Powdered formulation "BACTUCIDE-P" | |
|---|---|
| 4.0% | of the active component 15,000 IU/mg |
| 25.0% | aerosil (vesalon) |
| 5.0% | jugopon |
| 66.0% | china clay |

| Liquid formulation "BACTUCIDE-S" | |
|---|---|
| 8.0% | of the active component 6000 IU/mg |

| Liquid formulation "BACTUCIDE-S" | |
|---|---|
| 1.0% | carboxymethyl cellulose |
| 0.3 | emulgator |
| 3.0% | petrol-hydrocarbon |
| 87.7% | water |
| | pH 6, 8-7, 2 |

Formulation of BACTUCIDE-G granules 98.0% of granule (calcium carbonate)

2.0% of the active component (2.4 . $10^9$ spores/g)

The biologic insecticide "BACTUCIDE" is used especially against insects of the Lepidoptera group.

The quantity of liquid formulation of BACTUCIDE is 0.8–1.5 liters per ha, in that the dilution of this has to occur (before the use) in water quantity of 500–1000 liter. The dilution depends on the mode of application, the power of insects and the thickness of plants. The product can also be applied from air.

The powder formulation of BACTUCIDE-P has the same application as a liquid formulation in quantity of 0.6–1.0 kg/ha.

The formulation in form of granule (BACTUCIDE-G) is exclusively applied against insects Pyrausta nubilalis (corn). The quantity for application is 30 kg/ha.

BACTUCIDE is easily miscible and is compatible with chemical insecticides.

The examples of mixing the chemical insecticides with biologic insecticide BACTUCIDE are as follows:

Malathion 0.2% + Bactucide 0.12%

Dimethoate 0.1–0.2% + Bactucide 0.15%

Sevin 0.1–0.2% + Bactucide 0.15%

The same effects can be obtained with lower concentrations of chemical insecticide in that the toxicity is lowered. Also other chemical insecticides are compatible with Bactucide, as for example methylparathion, diazinon, DDT, Pyrethrum, Phosdrin etc.

We tested approximately 50 insects. The following tables list the insects sensitive to BACTUCIDE and the results obtained on these insects.

The activity of the liquid formulation of BACTUCIDE-S on some important insects.

Table 1.

| | The activity of BACTUCIDE on the on the insect *Trychoplusia ni* (cabbage). | | | |
|---|---|---|---|---|
| Quantity | % of killed larva TESTING in days | | | Total of larva |
| lit/ha | 1-5 | 5-7 | 10 | tested |
| 0.2 | 20 | 27 | 90 | 180 |
| 0.5 | 63 | 80 | 112 | 220 |
| 1.0 | 75 | 92 | 200 | 222 |
| Control | — | — | — | 650 |

Table 2.

| | The activity of BACTUCIDE on the insect *Hyponomeuta mallinellus* (apple). | | | |
|---|---|---|---|---|
| Quantity | Insectarium | | Field Tests | |
| lit/ha | % mortality corr. mort. | | % mort. | corr. mort. |
| 0.4 | 15 | 13.8 | 12 | 11.05 |
| 0.6 | 32 | 31.2 | 31 | 30.2 |
| 1.0 | 85 | 84.2 | 86.0 | 85.2 |
| 1.5 | 100 | 100 | 100 | 100 |

Table 3.

The activity of BACTUCIDE on the insect *Heliothis virescens* and *Heliothis zea* (tobacco and cotton).

| Concentration lit/ha | Days | Cotton % mortality | Tobacco % mortality |
|---|---|---|---|
| 0.2 | 4 | 30 | 75 |
| 0.5 | 6 | 50 | 100 |
| 1.0 | 8 | 95 | 100 |
| 1.5 | 10 | 100 | |

The activity of formulation of granule BACTUCIDE-G

Table 4.

The activity of BACTUCIDE-G on the insect *Pyrausta nubilalis* (corn).

| Material (formulation) | Dose kg/ha | N° plant | % of plant with living larva | Average N° of larva/plant | Effectiveness of BACTUCIDE-G in % |
|---|---|---|---|---|---|
| Bactucide-G | 30 | 80 | 41.0 | 0.9 | 82 |

We claim:

1. A method for the biosynthesis of a microbial insecticide containing spores and crystalline endotoxin, which comprises cultivating, by submerged cultivation, a Bacillus thuringiensis microoganism in a nutrient medium under formation of spores and preventing, by anaerobic shock, early lysis of the cells resulting during the course of the submerged cultivation by ventilation prior to the completion of spore formation.

2. A method according to claim 1, wherein the *Bacillus thuringiensis* is cultivated without lysis prior to the end of the formation of spores by interrupting the ventilation for 3 to 6 hours in the twelfth hour of cultivation and carrying out the cultivation under anaerobic conditions during that time.

* * * * *